(12) United States Patent
Xu et al.

(10) Patent No.: US 6,586,220 B1
(45) Date of Patent: Jul. 1, 2003

(54) **METHOD FOR CLONING AND EXPRESSION OF BSAWI RESTRICTION ENDONUCLEASE AND BSAWI METHYLASE IN *E. COLI***

(75) Inventors: Shuang-yong Xu, Lexington, MA (US); Jing Zhou, Beverly, MA (US); Adam Hume, Lewiston, ME (US); Robert Maunus, Danvers, MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 10/083,304

(22) Filed: Feb. 26, 2002

(51) Int. Cl.$^7$ .............................. C12N 9/22; C12N 15/54
(52) U.S. Cl. .............. 435/199; 435/320.1; 435/252.33; 536/23.2
(58) Field of Search .............................. 435/199, 320.1, 435/252.33; 536/23.2

(56) References Cited

U.S. PATENT DOCUMENTS

| 5,200,333 A | 4/1993 | Wilson .................... 435/172.3 |
| 5,498,535 A | 3/1996 | Fomenkov et al. ....... 435/172.3 |

OTHER PUBLICATIONS

Roberts and Macelis, Nucl. Acids Res. 29:268–269 (2001).
Kosykh et al., Mol. Gen. Genet. 178: 717–719, (1980).
Mann et al., Gene 3: 97–112, (1978).
Walder et al., Proc. Natl. Acad. Sci. 78: 1503–1507, (1981).
Bougueleret et al., Nucl. Acids Res. 12: 3659–3676. (1984).
Gingeras and Brooks, Proc. Natl. Acad. Sci. USA 80: 402–406, (1983).
Theriault and Roy, Gene 19: 355–359 (1982).
Blumenthal et al., J. Bacteriol. 164: 501–509, (1985).
Wayne et al. Gene 202: 83–88, (1997).
Kiss et al., Nucl. Acids Res. 13: 6403–6421, (1985).
Szomolanyi et al., Gene 10: 219–225, (1980).
Janulaitis et al., Gene 20: 197–204 (1982).
Kiss and Baldauf, Gene 21: 111–119, (1983).
Walder et al., J. Biol Chem. 258: 1235–1241, (1983).
Fomenkov et al., Nucl. Acids Res. 22: 2399–2403, (1994).
Malone et al., J. Mol. Biol. 253: 618–632, (1995).
New England Biolabs' Catalog, 2000–01, p. 220.
Kong, et al., Nucl. Acids. Res. 28:3216–3223 (2000).

*Primary Examiner*—Charles L. Patterson, Jr.
(74) *Attorney, Agent, or Firm*—Gregory D. Williams

(57) ABSTRACT

The present invention relates to recombinant DNA encoding the BsaWI restriction endonuclease as well as BsaWI methylase, expression of BsaWI restriction endonuclease and BsaWI methylase in *E. coli* cells containing the recombinant DNA.

6 Claims, 5 Drawing Sheets

FIG. 2A

```
      ATGACTAGACGATTACACATTATAGATTGTTTTTCTGGGCCTGGAGGAATCTGTACAGGA
   1  ------------------------------------------------------------+  60
      M  T  R  R  L  H  I  I  D  C  F  S  G  P  G  G  I  C  T  G
      TTTCGAGCAGCAGGATTTGAAACTTTATTAGCTATCGAGTTGGTAGAATCTTGTGTAGAA
  61  ------------------------------------------------------------+ 120
      F  R  A  A  G  F  E  T  L  L  A  I  E  L  V  E  S  C  V  E
      ACATATACGGCTAACCACAAAGATGTTCCTGTTATCAATAAAGATATCCGTGATGTAACT
 121  ------------------------------------------------------------+ 180
      T  Y  T  A  N  H  K  D  V  P  V  I  N  K  D  I  R  D  V  T
      GAAGAAGAGGTTAAGCGTATCGTAGGGAATCGTGTAGTGGATATACTTACAGCTGGAATG
 181  ------------------------------------------------------------+ 240
      E  E  E  V  K  R  I  V  G  N  R  V  V  D  I  L  T  A  G  M
      CCTTGCGAGACGTTTAGTACAGCGGGAGCAACTTCTCGTAGTTTCTATGATCATCGTCAG
 241  ------------------------------------------------------------+ 300
      P  C  E  T  F  S  T  A  G  A  T  S  R  S  F  Y  D  H  R  Q
      TTTTTATATCGTGAAGCTATTCGTCTTGCTGATGCTGTAAATGCACGGATGATTTTATTT
 301  ------------------------------------------------------------+ 360
      F  L  Y  R  E  A  I  R  L  A  D  A  V  N  A  R  M  I  L  F
      GAAAACGTTCCTGGTATCCAGACGAAGAAAGTGGCAAAAGATAGTGATCGTTTGATTATT
 361  ------------------------------------------------------------+ 420
      E  N  V  P  G  I  Q  T  K  K  V  A  K  D  S  D  R  L  I  I
      GATGAAATTTATGATGATTTAGCGAAATACGGATACGTTCACCATATATCTACGATATTA
 421  ------------------------------------------------------------+ 480
      D  E  I  Y  D  D  L  A  K  Y  G  Y  V  H  H  I  S  T  I  L
      AATGCAGAGGATTTTGGTGTTCCTCAATCAAGAGAGCGTTTTTTTATTTTAGCCAGTCGT
 481  ------------------------------------------------------------+ 540
      N  A  E  D  F  G  V  P  Q  S  R  E  R  F  F  I  L  A  S  R
      GAAAAATTGGATTTACGTGTTCCAGTTGCTAAAAACAGAAAAATTGTGACCGTAGAGGAA
 541  ------------------------------------------------------------+ 600
      E  K  L  D  L  R  V  P  V  A  K  N  R  K  I  V  T  V  E  E
      GCATTTATAGATTTACCTGAAGAACCGAAAGAAACGATTAATTCTGCAAAGAAGAAGCTA
 601  ------------------------------------------------------------+ 660
      A  F  I  D  L  P  E  E  P  K  E  T  I  N  S  A  K  K  K  L
      GAGAATGGAGAGGAAATTGAGGTAGAACAATATAAAGACATTGATTCTGCTTACAGCAAG
 661  ------------------------------------------------------------+ 720
      E  N  G  E  E  I  E  V  E  Q  Y  K  D  I  D  S  A  Y  S  K
      CTTATGAAGGATAGGGATTTCTGGAAGTTTGAGAAGAAAGAATTAGCATTGACATATCAT
 721  ------------------------------------------------------------+ 780
      L  M  K  D  R  D  F  W  K  F  E  K  K  E  L  A  L  T  Y  H
      TTCGCTCCTGTTCATCGAAAAGGGACTATCAAACGTTTTGAAATGATTAAACAGGGGGAA
 781  ------------------------------------------------------------+ 840
      F  A  P  V  H  R  K  G  T  I  K  R  F  E  M  I  K  Q  G  E
      GGATTGAAAGATCTATTCGATAAGTTGATGGCTGAACATGGACCTGAAGAAATCGAGCGG
 841  ------------------------------------------------------------+ 900
      G  L  K  D  L  F  D  K  L  M  A  E  H  G  P  E  E  I  E  R
```

FIG. 2B

```
          CTTCAGAAGGAGAAGATAATTCCAAATAAGTGGTATATCCAAAGAAATCGAAGATTATCT
  901     ---------+---------+---------+---------+---------+---------+ 960
           L  Q  K  E  K  I  I  P  N  K  W  Y  I  Q  R  N  R  R  L  S
          CCTGATAAGCCGAGCGTAACTGTAACATCACATTGTTTAAGCGAGTTGGTTCATCCGATC
  961     ---------+---------+---------+---------+---------+---------+ 1020
           P  D  K  P  S  V  T  V  T  S  H  C  L  S  E  L  V  H  P  I
          AAAAATCGAGCATTGACGATTCGTGAGGTTGCACGTTTGCAAAGTTTTCCTGATTTCTAT
 1021     ---------+---------+---------+---------+---------+---------+ 1080
           K  N  R  A  L  T  I  R  E  V  A  R  L  Q  S  F  P  D  F  Y
          GATTTCAAAGGCGGAAAATTTGTAGCACCTCATAAAGACCCACAACAGGATAAATATGAA
 1081     ---------+---------+---------+---------+---------+---------+ 1140
           D  F  K  G  G  K  F  V  A  P  H  K  D  P  Q  Q  D  K  Y  E
          CAGATTGGGGATGCCGTGCCTCCTTTGTTGGCTTATCATTGGGGGCTGGTTATAAAAGAA
 1141     ---------+---------+---------+---------+---------+---------+ 1200
           Q  I  G  D  A  V  P  P  L  L  A  Y  H  W  G  L  V  I  K  E
          ATTCTTGAAGGAGTTAAAGTTACGGAGGGGGTCTAG
 1201     ---------+---------+---------+------  1236
           I  L  E  G  V  K  V  T  E  G  V  *
```

FIG. 3

```
    ATGAATTTTTTTGAGTATTGTATCAGCACCTATGCCAAGATATTTGAAGAAACGATGAAT
  1 ------------+---------+---------+---------+---------+---------+  60
    M  N  F  F  E  Y  C  I  S  T  Y  A  K  I  F  E  E  T  M  N
    GCAGTGGGTGATGAACGAGTTTCGCAAAAAAAGGCAATCCGTGACACAATGATCTCAGCT
 61 ------------+---------+---------+---------+---------+---------+ 120
    A  V  G  D  E  R  V  S  Q  K  K  A  I  R  D  T  M  I  S  A
    ATGAGAGAGTTTCCAAATGTCGAAGCGGCTGAAATCTGGAAAGCTGTGTATTCAGCCCAT
121 ------------+---------+---------+---------+---------+---------+ 180
    M  R  E  F  P  N  V  E  A  A  E  I  W  K  A  V  Y  S  A  H
    ATGGATCGTAAATCAGGTATAGCAGACCCAGATATTATTCAAAAGGTCATATCAGCGGAG
181 ------------+---------+---------+---------+---------+---------+ 240
    M  D  R  K  S  G  I  A  D  P  D  I  I  Q  K  V  I  S  A  E
    AATAGCTGGAAAAAAATCCAGTGGACATGCCTTTGAGGAAATGATTAAACTACTAGGGAAT
241 ------------+---------+---------+---------+---------+---------+ 300
    N  S  W  K  K  S  S  G  H  A  F  E  E  M  I  K  L  L  G  N
    AGCAGTTTAGAAGAATATGGAATGCGTATTTTGCTCCAAAAAGACTTAAACATGATGATT
301 ------------+---------+---------+---------+---------+---------+ 360
    S  S  L  E  E  Y  G  M  R  I  L  L  Q  K  D  L  N  M  M  I
    GAAAACCAAGAGATTGCAAATGAACCACGCGACATAAATTGGTTAAAAGAGCAAATTTCT
361 ------------+---------+---------+---------+---------+---------+ 420
    E  N  Q  E  I  A  N  E  P  R  D  I  N  W  L  K  E  Q  I  S
    TCTAACGTATTTGATTTGTACATTACAGTGCGGAATAACGACAAAGAGTATGTGTTTGGC
421 ------------+---------+---------+---------+---------+---------+ 480
    S  N  V  F  D  L  Y  I  T  V  R  N  N  D  K  E  Y  V  F  G
    TGCATTCAATCGAAAACAAGCATACGCGATAGAGTCACCCGTGACCGTGAGCCTTCGATG
481 ------------+---------+---------+---------+---------+---------+ 540
    C  I  Q  S  K  T  S  I  R  D  R  V  T  R  D  R  E  P  S  M
    AAGGCGATGGAAGCTTTCTTTTGGTCAGTTGCTATCTGTTTAGATGGAGACTTTTTAAAA
541 ------------+---------+---------+---------+---------+---------+ 600
    K  A  M  E  A  F  F  W  S  V  A  I  C  L  D  G  D  F  L  K
    ATGCCAAAATTTATCGCAATGGTAAATGGAGGAACAAGTAATTATAGATTGAATGGCTGG
601 ------------+---------+---------+---------+---------+---------+ 660
    M  P  K  F  I  A  M  V  N  G  G  T  S  N  Y  R  L  N  G  W
    CATGGTATGTATGTATTTTGGGACAAGCCAACGATTGATCGTATTTATCCGATTGATATC
661 ------------+---------+---------+---------+---------+---------+ 720
    H  G  M  Y  V  F  W  D  K  P  T  I  D  R  I  Y  P  I  D  I
    AACCTTGAATTGTTTGTACAACATGCACGTGAGGCAGCAGAGGATTGGCTACATAGACGG
721 ------------+---------+---------+---------+---------+---------+ 780
    N  L  E  L  F  V  Q  H  A  R  E  A  A  E  D  W  L  H  R  R
    CAATGGTTTAATTATGAGTGGAAAGCAGGACAAAAATAA
781 ------------+---------+---------+--------  819
    Q  W  F  N  Y  E  W  K  A  G  Q  K  *
```

METHOD FOR CLONING AND EXPRESSION OF BSAWI RESTRICTION ENDONUCLEASE AND BSAWI METHYLASE IN *E. COLI*

BACKGROUND OF THE INVENTION

The present invention relates to recombinant DNA that encodes the BsaWI restriction endonuclease (BsaWI endonuclease or BsaWI) as well as BsaWI methyltransferase (BsaWI methylase or M.BsaWI), expression of BsaWI endonuclease and methylase in *E. coli* cells containing the recombinant DNA.

BsaWI endonuclease is found in the strain of *Bacillus stearothermophilus* W1718 (New England Biolabs' strain collection). It recognizes the double-stranded DNA sequence 5'W/CCGGW3' (W=A or T, / indicates the cleavage position) and cleaves between the W and C to generate 4-base cohesive ends. BsaWI methylase (M.BsaWI) is also found in the same strain, which recognizes the same DNA sequence and presumably modifies the cytosine at the C5 position on hemi-methylated or non-methylated BsaWI sites.

Type II restriction endonucleases are a class of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind particular sequences of nucleotides (the 'recognition sequence') along the DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. Over two hundred and twenty-eight restriction endonucleases with unique specificities have been identified among the many hundreds of bacterial species that have been examined to date (Roberts and Macelis, Nucl. Acids Res.29:268–269 (2001)).

Restriction endonucleases typically are named according to the bacteria from which they are discovered. Thus, the species *Deinococcus radiophilus* for example, produces three different restriction endonucleases, named DraI, DraII and DraIII. These enzymes recognize and cleave the sequences 5'TTT/AAA3', 5'PuG/GNCCPy3' and 5'CACNNN/GTG3' respectively. *Escherichia coli* RY13, on the other hand, produces only one enzyme, EcoRI, which recognizes the sequence 5'G/AATTC3'.

A second component of bacterial/viral restriction-modification (R-M) systems are the methylase. These enzymes co-exist with restriction endonucleases and they provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiably foreign DNA, is sensitive to restriction endonuclease recognition and cleavage. During and after DNA replication, usually the hemi-methylated DNA (DNA methylated on one strand) is also resistant to the cognate restriction digestion.

With the advancement of recombinant DNA technology, it is now possible to clone genes and overproduce the enzymes in large quantities. The key to isolating clones of restriction endonuclease genes is to develop an efficient method to identify such clones within genomic DNA libraries, i.e. populations of clones derived by 'shotgun' procedures, when they occur at frequencies as low as $10^{-3}$ to $10^{-4}$. Preferably, the method should be selective, such that the unwanted clones with non-methylase inserts are destroyed while the desirable rare clones survive.

A large number of type II restriction-modification systems have been cloned. The first cloning method used bacteriophage infection as a means of identifying or selecting restriction endonuclease clones (EcoRII: Kosykh et al., Mol. Gen. Genet. 178: 717–719, (1980); HhaII: Mann et al., Gene 3: 97–112, (1978); PstI: Walder et al., Proc. Nat. Acad. Sci. 78: 1503–1507, (1981)). Since the expression of restriction-modification systems in bacteria enables them to resist infection by bacteriophages, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into *E. coli* cloning vectors (EcoRV: Bougueleret et al., Nucl. Acids. Res. 12: 3659–3676, (1984); PaeR7: Gingeras and Brooks, Proc. Natl. Acad. Sci. USA 80: 402–406, (1983); Theriault and Roy, Gene 19: 355–359 (1982); PvuII: Blumenthal et al., J. Bacteriol. 164: 501–509, (1985); Bsa45I: Wayne et al. Gene 202:83–88, (1997)).

A third approach is to select for active expression of methylase genes (methylase selection) (U.S. Pat. No. 5,200,333 and BsuRI: Kiss et al., Nucl. Acids. Res. 13:6403–6421, (1985)). Since restriction-modification genes are often closely linked together, both genes can often be cloned simultaneously. This selection does not always yield a complete restriction system however, but instead yields only the methylase gene (BspRI: Szomolanyi et al., Gene 10: 219–225, (1980); BcnI: Janulaitis et al., Gene 20: 197–204 (1982); BsuRI: Kiss and Baldauf, Gene 21: 111–119, (1983); and BsaI: Walder et al., J. Biol. Chem. 258: 1235–1241, (1983)).

A more recent method, the "endo-blue method", has been described for direct cloning of thermostable restriction endonuclease genes into *E. coli* based on the indicator strain of *E. coli* containing the dinD::lacZ fusion (U.S. Pat. No. 5,498,535; Fomenkov et al., Nucl. Acids Res. 22:2399–2403, (1994)). This method utilizes the *E. coli* SOS response signals following DNA damage caused by restriction endonucleases or non-specific nucleases. A number of thermostable nuclease genes (TaqI, Tth111I, BsoBI, Tf nuclease) have been cloned by this method (U.S. Pat. No. 5,498,535). The disadvantage of this method is that some positive blue clones containing a restriction endonuclease gene are difficult to culture due to the lack of the cognate methylase gene.

There are three major groups of DNA methyltransferases based on the position and the base that is modified (C5 cytosine methylases, N4 cytosine methylases, and N6 adenine methylases). N4 cytosine and N6 adenine methylases are amino-methyltransferases (Malone et al. J. Mol. Biol. 253:618–632, (1995)). When a restriction site on DNA is modified (methylated) by the methylase, it is resistant to digestion by the cognate restriction endonuclease. Sometimes methylation by a non-cognate methylase can also confer DNA sites resistant to restriction digestion. For example, Dcm methylase modification of 5' CCWGG 3' (W=A or T) can also make the DNA resistant to PspGI restriction digestion. Another example is that CpM methylase can modify the CG dinucleotide and make the NotI site (5'GCGGCCGC3') refractory to NotI digestion (New England Biolabs'Catalog, 2000–01, page 220; Beverly, Mass.). Therefore methylases can be used as a tool to modify certain DNA sequences and make them uncleavable by restriction enzymes.

Type II methylase genes have been found in many sequenced bacterial genomes (GenBank, http://www.ncbi.nlm.nih.gov; and Rebase, http://rebase.neb.com/rebase). Direct cloning and over-expression of ORFs adjacent to the methylase genes yielded restriction enzymes with novel specificities (Kong et al. Nucl. Acids Res. 28:3216–3223 (2000)). Thus microbial genome mining emerged as a new way of screening/cloning new type II restriction enzymes and methylases and their isoschizomers.

Because purified restriction endonucleases and modification methylases are useful tools for creating recombinant molecules in the laboratory, there is a strong commercial interest to obtain bacterial strains through recombinant DNA techniques that produce large quantities of restriction enzymes and methylases. Such over-expression strains should also simplify the task of enzyme purification.

SUMMARY OF THE INVENTION

The present invention relates to a method for cloning BsaWI restriction gene (bsaWIR) from *Bacillus stearothermophilus* W1718 into *E. coli* by inverse PCR and direct PCR from genomic DNA using primers that were based on the DNA sequences obtained via methylase selection.

The difficulty was to express bsaWIR gene in *E. coli* using high-copy-number expression vector such as pRRS or medium-copy-number vector such as pET21at. When a PCR fragment containing the bsaWIR gene was inserted in pRRS or pET21at and transformed pre-modified *E. coli* strain ER2502 [pLG339-BsaWIM], clones with inserts were found, but low BsaWI endonuclease activity was detected in IPTG-induced cell extracts. This negative result indicated there was selection pressure to isolate endonuclease mutants.

Since expression from a high/medium-copy-number vectors did not generate a stable high expression clone, efforts were made to express the bsaWIR gene in a low-copy-number plasmid pACYC-T7at. The tightly regulated T7 expression vector pACYC-T7at contains four transcription terminators inserted before the T7 promoter to reduce basal level expression. The successful expression strategy was to express bsaWIM gene in a high-copy-number plasmid pRRS and bsaWIM gene in a low-copy-number T7 vector within the same *E. coli* host.

BRIEF DESCRIPTION OF THE DRAWINGS

FIG. 2. BsaWI methylase gene sequence (bsaWIM, 1236 bp) (SEQ ID NO:1) and the encoded amino acid sequence (SEQ ID NO:2).

FIG. 3. BsaWI endonuclease gene sequence (bsaWIR, 819 bp) (SEQ ID NO:3) and the encoded amino acid sequence (SEQ ID NO:4).

DETAILED DESCRIPTION OF THE INVENTION

Figure 1:
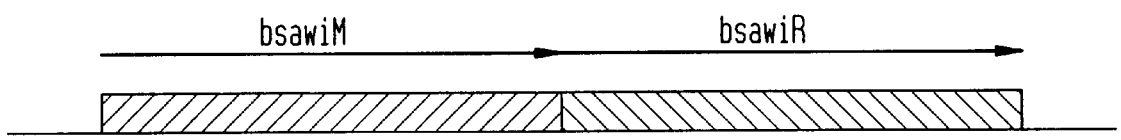
FIG. 1. Gene organization of BsaWI R-M system. bsaWIR, BsaWI restriction endonuclease gene; bsaWIM, BsaWI methylase gene.

It proved very difficult to express bsaWIR gene in *E. coli* using high-copy-number expression vector such as pRRS or medium-copy-number vector such as pET21at. When a PCR fragment containing the bsaWIR gene was inserted in pRRS and transformed pre-modified *E. coli* strain ER2502 [pLG339-BsaWIM], many clones with inserts were found, but very low BsaWI endonuclease activity was detected in IPTG-induced cell extracts. This negative result suggested there was selection pressure to isolate endonuclease mutants with reduced activity. This was probably due to under-methylation by M.BsaWI on the host chromosome or lower specific activity of M.BsaWI at 37° C. than the physiological temperature of 60° C. The native strain has an optimal temperature of 60° C.

Since expression from a high-copy-number vector did not generate a stable high expression clone, efforts were made to express the bsaWIR gene in a medium-copy-number plasmid pET21at. The tightly regulated T7 expression vector pET21at contains four transcription terminators inserted before the T7 promoter to reduce basal level expression.

The bsaWIR gene was amplified in PCR from genomic DNA. Following purification and ethanol precipitation, the PCR DNA was digested with XbaI and XhoI and ligated to pET21at with compatible ends. The ligated DNA was transferred into pre-modified host ER2566 [pLG339-BsaWIM]. After screening 34 plasmids from Ap$^R$ Km$^R$ co-transformants, 7 clones were found to carry the PCR insert. These 7 clones were cultured and induced with IPTG. Cells were harvested and lysed by sonication. Clarified cell lysates were assayed for BsaWI activity on λ DNA. Three extracts generated BsaWI digestion pattern and one extract gave rise to partial digestion. The rest of three did not contain any activity. The recombinant BsaWI activity was relatively low (~5,000 units/g wet cells), probably resulting from mutations introduced in PCR. Recombinant BsaWI activity was detected only in undiluted cell extract. Partial activity was observed after 10 and 20-fold dilution of the cell extracts.

The successful expression strategy was to express bsaWIM gene in a high-copy-number plasmid pRRS and bsaWIR gene in a low-copy-number T7 vector within the same *E. coli* host. The method described herein by which the bsaWIM and bsaWIR genes are preferably cloned and expressed in *E. coli* include the following steps:

1. Preparation of Genomic DNA, Restriction Digestion, and Construction of Genomic DNA Library Genomic DNA was prepared from *Bacillus stearothermophilus* W1718 by the standard method.

ApoI and NlaIII were used to partially digest genomic DNA. The partially digested DNA was purified and ligated to EcoRI and SphI digested and CIP treated pRRS vector that contains multiple BsaWI sites. The ligated DNA was used to transform ER2502 by electroporation. Approximately 10,000 Ap$^R$ transformants were obtained for both partial libraries. All the colonies were pooled and amplified. Plasmid DNA was prepared, generating a mixed library.

2. Cloning of bsaWIM Gene by Methylase Selection

The primary plasmid library DNA was challenged with BsaWI. The digested DNA was transferred into ER2502 by transformation, resulting in six Ap$^R$ survivors. Plasmid DNA was prepared and following BsaWI digestion one resistant and one partial resistant clone were found.

3. Restriction Mapping and Subcloning of the Insert

The resistant clone DNA was digested with a number of restriction enzymes to estimate the insert size. The insert size was estimated to be 3.7 to 4.2 kb. The BamHI, EcoRV, HindIII, and PvuII fragments were gel-purified and subcloned into pUC19. The entire inserts were sequenced. One open reading frame (ORF) of 1236 bp was found that has extensive homology to other C5 methylases. This ORF was named bsaWIM gene.

4. Inverse PCR Amplification of DNA Downstream of BsaWI Methylase

After identification of the methylase gene, efforts were made to clone adjacent DNA. One truncated ORF was found downstream of the bsaWIM gene. DNA sequence at the C-terminus of bsaWIM gene was used as the template for inverse PCR.

The genomic DNA was digested with restriction enzymes, purified, and self-ligated. The circular DNA molecules were used as templates for inverse PCR. PCR products were found in the BspHI, DpnII, NlaIII, and TfiI templates. The PCR products were purified from a low-melting agarose gel, treated with β-agarase, precipitated with ethanol, and sequenced directly with primers. The BspHI, DpnII, NlaIII, and TfiI PCR fragments generated about 1700 bp, 250 bp, 275 bp, and 1340 bp new sequences, respectively. Therefore, the entire BspHI fragment was sequenced with four additional primers. After sequencing about 1.1 kb, an ORF with 819 bp long was found downstream of the bsaWIM gene. This gene was most likely the restriction gene (bsaWIR) coding for BsaWI endonuclease. Transcription of M and R genes is oriented in the same direction (see FIG. 1 for gene organization).

5. Expression of bsaWIR Gene in E. coli

The successful cloning/expression strategy was to express bsaWIM gene in a high-copy-number plasmid pRRS and the bsaWIR gene in a low-copy-number T7 vector.

Figure 4:
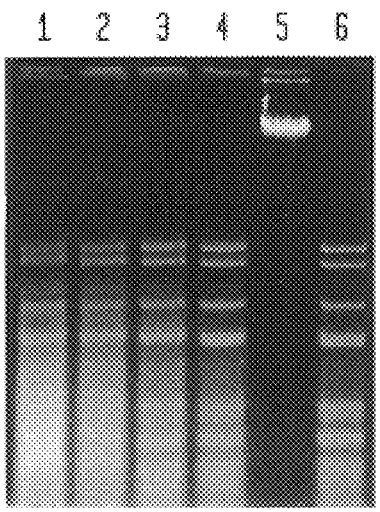
FIG. 4. Recombinant BsaWI endonuclease activity in cell extract. λ DNA was used as the substrate. Lanes 1–4, 1×, ½, ⅕, ⅒, diluted cell extract added in the restriction digestions. Lanes 5 and 6, λ DNA and λ DNA digested with native BsaWI.
Figure 5:
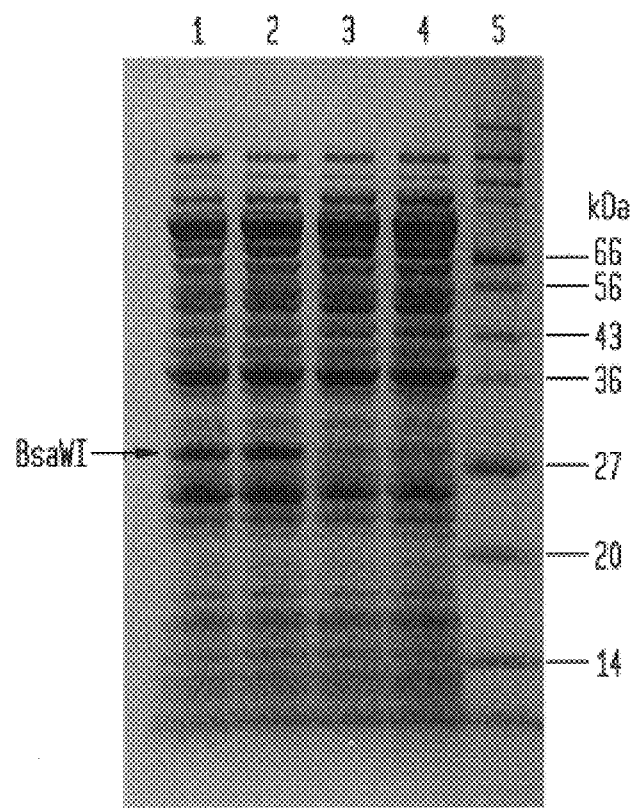
FIG. 5. Recombinant BsaWI protein analyzed on SDS-PAGE. Lanes 1 and 2, recombinant BsaWI clone #3; lanes 3 and 4, heated cell extract; lane 5, protein size marker. Arrow indicates IPTG-induced BsaWI endonuclease. The predicted molecular mass of BsaWI endonuclease is 31.9 kDa. The apparent molecular wight of BsaWI endonuclease on SDS-PAGE gel was 30 kDa.

The plasmid pRRS-BsaWIM was the original methylase positive clone isolated from methylase selection. Plasmid pRRS-BsaWIM was transferred into ER2566 to premodify E.coli host. The bsaWIR gene was amplified from genomic DNA by PCR with Vent® DNA polymerase. Following purification and digestion with BamHI, it was ligated to CIP-treated pACYC-T7at with compatible ends. The ligated DNA was transferred into pre-modified host ER2566 [pRRS-BsaWIM] by transformation. Ten ml of cell cultures were made from individual transformants and target protein production induced with IPTG. Cell extracts were prepared and assayed for BsaWI endonuclease activity on λ DNA substrate. Six highly active BsaWI-producing clones were found after screening 20 IPTG-induced cell extracts. The BsaWI activity of one active clone was shown in FIG. 4. The cell extract of active clone #3 was heated at 60° C. for 30 min and heat-denatured E. coli proteins were removed by centrifugation. The remaining proteins were analyzed by SDS-PAGE. One induced protein of approximately 30 kDa apparent size was detected, in close agreement with the predicted size of 31.9 kDa.

In order to find out the exact start codon of the native protein, the native BsaWI endonuclease was purified from the native B. Stearothermophilus W1718 strain. The N-terminus of purified native protein was sequenced. The actual amino acid sequence is consistent with the predicted amino acid sequence from the coding DNA sequence. In addition, expression of a deletion mutant with 18 amino acid deletion generated an inactive protein. This deletion mutant started from the second ATG codon in the coding sequence.

The plasmid DNA pACYC-T7ter-BsaWIR clone #3 was prepared by Qiagen column and the entire insert was sequenced. It was found that the insert contained the wild type coding sequence.

EXAMPLE 1

Cloning of BsaWI Restriction-modification System in E. coli

1. Preparation of Genomic DNA

Genomic DNA was prepared from 5 g of *Bacillus stearothermophilus* W1718 (NEB#797, New England Biolabs strain collection, Beverly, Mass.) by the standard procedure consisting of the following steps:

a. Cell lysis by addition of lysozyme (2 mg/ml final), sucrose (1% final), and 50 mM Tris-HCl, pH 8.0.

b. Further cell lysis by addition of SDS at a final concentration of 0.1%.

c. Further cell lysis by addition of 1% Triton X-100, 62 mM EDTA, 50 mM Tris-HCl, pH 8.0.

d. Removal of proteins by phenol-CHCl$_3$ extraction of DNA 3 times (equal volume) and CHCl$_3$ extraction once.

e. Dialysis in 4 liters of TE buffer, buffer change twice.

f. RNase A treatment to remove RNA.

g. Genomic DNA precipitation in 95% ethanol, centrifuged, washed, dried and resuspended in TE buffer.

2. Restriction digestion of genomic DNA and construction of genomic DNA library

Varying units of restriction enzymes ApoI and NlaIII were used to digest 25 μg genomic DNA (ApoI: 12, 8, and 4 units; NlaIII, 10, 5, 2, 1 units) to achieve limited partial digestion. The partially digested DNA was purified via phenol-CHCl$_3$ extraction and ethanol precipitation. The ApoI and NlaIII digested DNA were ligated to EcoRI and SphI digested and CIP treated pRRS vector that contains multiple BsaWI sites. The vector pRRS is a high-copy-number plasmid for cloning and expression of genes in E. coli. Following overnight ligation, the ligated DNA was used to transform an endA$^-$ RR1 competent cells (ER2502, NEB's collection) by electroporation. Approximately 10,000 Ap$^R$ transformants were obtained for both partial libraries. All the colonies were pooled and amplified in 1 liter LB+Ap overnight. Plasmid DNA was prepared by Qiagen Maxi-prep columns, resulting in a mixed library.

2. Cloning of bsaWIM Gene by Methylase Selection

The primary plasmid DNA library (1 μg, 2 μg, and 4 μg DNA) was challenged with 50 units of BsaWI digestion at 60° C. overnight. The digested DNA was transferred into ER2502 by transformation, resulting in six Ap^R survivors. Plasmid DNA was prepared by Qiagen spin columns from 1.5 ml overnight cell cultures. After digestion with BsaWI, one true resistant clone (#4), and one partial resistant clone were found (#6).

3. Restriction Mapping and Subcloning of the Insert

Clone #4 was digested with restriction enzymes BamHI, BglII, EcoRI, EcoRV, HindIII, HpaI, HincII, PstI, PvuII, SphI, XbaI, and XhoI, respectively. The insert size was estimated to be 3.7 to 4.2 kb. The BamHI, EcoRV, HindIII, and PvuII fragments were gel-purified from low melting agarose gel and cloned into pUC19. Inserts were sequenced using pUC universal forward and reverse primers and custom-made primers. DNA sequencing was performed using the dye terminator sequencing kit from PE Biosystems. One open reading frame (ORF) of 1236 bp was found that has extensive homology to other C5 methylases. This ORF was named bsaWIM gene. Later it was confirmed that expression of this gene conferred the plasmid resistant to BsaWI digestion.

4. Inverse PCR Amplification of DNA Downstream of BsaWI Methylase

After identification of the methylase gene, efforts were made to clone adjacent DNA. One truncated ORF was found downstream of the bsaWIM gene. The start codon of the downstream ORF is immediately after the TAG stop codon of bsaWIM gene. Within this truncated ORF there is an ApoI site right after three codons. Since this clone may be derived from ApoI partial library, the sequence after the ApoI site could be random genomic DNA fragments ligated to the bsaWIM gene, efforts were made to obtain the downstream sequence by inverse PCR and direct sequencing of the PCR products. DNA sequence at the C-terminus of bsaWIM gene was used as the template for primer design.

Two primers were synthesized with the following sequences:
5'cggcatccccaatctgttcatatt3' (219-118) (SEQ ID NO:5)
5'tgcctcctttgttggcttatcatt3' (219-119) (SEQ ID NO:6)

The genomic DNA was digested with BamHI, BglII, BspHI, BstYI, DpnII, HaeII, MseI, NlaIII, NspI, Sau3AI, and TaqI, respectively in appropriate restriction buffers. The digested DNA was purified through Qiagen spin columns. Self-ligation was set up at a low DNA concentration at 2 µg/ml overnight at 16° C. T4 DNA ligase was inactivated at 65° C. for 30 min and the circular DNA was precipitated in ethanol and used as the template for inverse PCR. PCR conditions were 94° C. for 2 min, 1 cycle; 94° C. for 1 min, 60° C. for 1 min, 72° C. for 2 min for 35 cycles. PCR products were found in the BspHI, DpnII, NlaIII, and TfiI templates. The PCR products were purified from a 1% low-melting agarose gel, treated with β-agarase for 2 h, precipitated with ethanol, and sequenced directly with primers 219-118 and 119. The BspHI, DpnII, NlaIII, and TfiI PCR fragments generated about 1700 bp, 250 bp, 275 bp, and 1340 bp new sequences, respectively. Considering that type II restriction gene is usually less than 1.5 kb, the BspHI fragment should contain the entire endonuclease gene. Therefore, the entire fragment was sequenced with four additional primers. The sequencing primers have the following sequences:
5'ctgtacagattcctccaggcccag3' (221-66) (SEQ ID NO:7)
5'taatgtgtaatcgtctagtcatga3' (221-67) (SEQ ID NO:8)
5'tgtacattacagtgcggaataacg3' (221-68) (SEQ ID NO:9)
5'tatgtgtttggctgcattcaatcg3' (221-69) (SEQ ID NO:10)

After sequencing about 1.1 kb, an ORF with 819 bp long was found downstream of the bsaWIM gene. This gene was most likely the restriction gene (bsaWIR) coding for BsaWI endonuclease. Transcription of M and R genes is oriented in the same direction. They are arranged in head-to-tail fashion (see FIG. 1 for gene organization).

EXAMPLE 2

Expression of bsaWIR Gene in E. coli

In order to express bsaWIR and bsaWIM genes together in the same cell, the bsaWIM gene was first amplified from genomic DNA in a PCR reaction and cloned into a low copy number plasmid pLG339 with pSC101 origin and Km^R selection marker. The PCR primers have the following sequences:
5'gtgggatccatgactagacgattacacattatagat3' (244-44, underlined nt, BamHI site) (SEQ ID NO:11)
5'tgatacgcatgcctagaccccctccgtaactttaactcc3' (244-45, underlined nt, SphI site) (SEQ ID NO:12)

PCR conditions were 95° C. for 2 min, 1 cycle; 95° C. for 30 sec, 60° C. for 30 sec, 72° C. 1 min for 25 cycles. The PCR product was digested with BamHI and SphI overnight at 37° C., purified by running through spin,columns and ligated to CIP treated pLG339 with compatible ends. Following ligation overnight, the DNA was transferred into ER2502 by transformation. After screening 22 plasmids isolated from individual Km^R transformants and BsaWI digestion, seven BsaWI-resistant clones were detected. The pre-modified host ER2502 [pLG339-BsaWIM] was used for over-expression of BsaWI endonuclease.

Two PCR primers were synthesized for PCR amplification of the bsaWIR gene.
5'gaaggagcatgcggaggtaaataaatgaatttttttgagtattgtatcagc3' (266-127, underlined nt, SphI site) (SEQ ID NO:13)
5'gccggatccagacataggttgaacatctaattatta3' (266-128, underlined nt, BamHI site) (SEQ ID NO:14)

PCR conditions were 95° C. 2 min, 1 cycle; 95° C. for 30 sec, 60° C. for 30 sec, 72° C. for 1 min for 20 cycles with Vent® DNA polymerase. Since Vent® DNA polymerase is sensitive to $Mg^{++}$ concentration and generates variable product yield, efforts were made to optimize the PCR condition with the addition of extra $MgSO_4$. It was found that 2 mM $MgSO_4$ yielded very little PCR products whereas in 5 and 6 mM $MgSO_4$ there were large amounts of PCR products. It was concluded that 5 mM was the optimal $Mg^{++}$ concentration for amplification of the bsaWIR gene from genomic DNA. More PCR DNA containing bsaWIR gene was amplified from genomic DNA and purified by phenol-$CH_3Cl$ extraction and $CH_3Cl$ extraction, precipitated with ethanol, dried and resuspended in TE buffer. Following restriction digestion with BamHI and SphI and purification through Qiagen spin columns, the PCR DNA was ligated to pRRS with compatible ends. The ligated DNA was transformed into pre-modified host ER2502 [pLG339-BsaWIM] and AP^R Km^R transformants were selected at 30° C. to reduce the plasmid copy nubmer. After screening 36 plasmids from the co-transformants, 16 clones were found to contain inserts. Ten ml cell cultures were grown for 4–5 h at 30° C. and IPTG was added to a final concentration of 0.5 mM. After 3 h IPTG induction, cells were harvested by centrifugation and resuspended in 1 ml sonication buffer (50 mM Tris-HCl, pH 8, 5 mM EDTA, 50 mM NaCl). Cells were lysed by sonication and cell debris removed by centrifugation. Two µl of cell lysate was assayed on λ DNA for BsaWI activity. Partial BsaWI activity was detected in 3 samples. Although λ DNA was digested to smaller fragments, no distinct BsaWI digestion pattern was observed which might be caused by further digestion with non-specific exonuclease. Since pRRS-BsaWIR clones did not give rise to high expression, a second strategy was to clone the bsaWIR gene into a tightly-controlled T7 expression vector pET21at (four transcription terminators inserted before the T7 promoter to reduce basal level expression).

A set of PCR primers was made with the following sequence:
5'gaaggatctagaggatccggaggtaaataaatgaattttttgagtattgtatc3'
(247-50, underlined nt, XbaI site) (SEQ ID NO:15)
5'caatttctcgagagacataggttgaacatctaattatta3' (247-51, underlined nt, XhoI site) (SEQ ID NO:16)

PCR conditions were 95° C. 2 min, 1 cycle; 95° C. for 30 sec, 60° C. for 30 sec, 72° C. for 1 min for 20 cycles with Vent® DNA polymerase. The bsaWIR gene was amplified in PCR from genomic DNA. Following purification by phenol-CH₃Cl extraction and ethanol precipitation, the PCR DNA was digested with XbaI and XhoI and ligated to pET21at with compatible ends. The ligated DNA was transferred into pre-modified host ER2566 [pLG339-BsaWIM]. After screening 34 plasmids from Ap$^R$ Km$^R$ co-transformants, 7 clones were found to carry the PCR insert. These 7 clones were cultured in 10 ml LB Ap (100 μg/ml) and Km (50 μg/ml) for 4 h at 37° C. and induced with IPTG (final concentration at 0.5 mM) for 3 h. Cells were harvested and lysed by sonication. Clarified cell lysates were assayed for BsaWI activity on λ DNA. Three cell extracts generated BsaWI digestion pattern and one sample gave rise to partial digestion. The rest of three did not display any activity. The recombinant BsaWI activity was relatively low (~5,000 units/g wet cells), probably resulted from mutations introduced in PCR. Recombinant BsaWI activity was detected only in 1× cell extract. Partial activity was observed after 10 and 20-fold dilution of the cell extracts.

To further increase the expression of BsaWI endonuclease, a third strategy was employed in which the methylase gene was expressed from a high-copy-number plasmid and the endonuclease gene was expressed from a low-copy-number T7 vector.

The plasmid pRRS-BsaWIM was the original methylase positive clone isolated from methylase selection. Plasmid pRRS-BsaWIM was transferred into ER2566 to premodify E. coli host. The plasmid DNA re-isolated from ER2566 was fully resistant to BsaWI digestion, indicating full modification of BsaWI sites on the plasmid. One forward PCR primer was made with the following sequence which contains the ribosome binding site GGAGGT six-base before the start codon:
5'ccggggatccggaggtaaataaatgaattttttgagtattgtatcagcacc3'
(273-138, underlined nt, BamHI site) (SEQ ID NO:17)
The reverse primer is the same as primer 266-128.

The bsaWIR gene was amplified from genomic DNA by PCR under condition of 95° C. 2 min, 1 cycle; 94° C. for 30 sec, 55° C. for 30 sec, 72° C. for 2 min for 20 cycles with Vent® DNA polymerase. Following purification by phenol-CH₃Cl extraction and ethanol precipitation, the PCR DNA was digested with BamHI and ligated to CIP-treated pACYC-T7at with compatible ends. The ligated DNA was transferred into pre-modified host ER2566 [pRRS-BsaWIM] by transformation. Co-transformants were plated on LB agar plates with Ap (100 μg/ml) and Cm (33 μg/ml). Ten ml of cell cultures were made from individual transformants and grown to late log phase in LB supplemented with Ap and Cm (~4 h at 37° C.). IPTG was added to the final concentration of 0.5 mM to induce expression of the target gene. After 3 h induction, cells were harvested by centrifugation and cell extracts were prepared by sonication. Clarified lysate was assayed for BsaWI endonuclease activity on λ DNA substrate and then analyzed by agarose gel electrophoresis. Six highly active BsaWI-producing clones were found after screening 20 IPTG-induced cell extracts. Seven partially active BsaWI-producing clones were also found, suggesting mutation(s) may have been introduced during PCR. The BsaWI activity of one active clone was shown in FIG. 4. The cell extract of active clone #3 was heated at 60° C. for 30 min and heat-denatured E. coli proteins were removed by centrifugation. The remaining proteins were analyzed by SDS-PAGE. One induced protein of approximately 30 kDa apparent size was detected, in close agreement with the predicted size of 31.9 kDa. It was confirmed that the ORF adjacent to bsaWIM gene is the bona fide bsaWIR gene, encoding active BsaWI endonuclease. The recombinant BsaWI endonuclease yield was ~10$^5$ units/g of wet cells from the over-producing strain.

In order to find out the exact start aa (codon) of the native protein, the native BsaWI endonuclease was purified from B. Stearothermophilus W1718 strain. The N-terminus of purified protein was sequenced. The actual amino acid sequence is consistent with the predicted amino acid sequence from the coding DNA sequence. In addition, expression of a deletion mutant with 18 aa deletion generated an inactive protein. This deletion mutant started from the second ATG codon in the coding sequence.

The plasmid DNA pACYC-T7ter-BsaWIR clone #3 was prepared by Qiagen mini-spin column and the entire insert was sequenced. It was found that the insert contained the wild type coding sequence.

The strain NEB#1438, ER2566 [pRRS-BsaWIM, pACYC-T7ter-BsaWIR] has been deposited under the terms and conditions of the Budapest Treaty with the American Type Culture Collection on Mar. 17, 2002 and received ATCC Accession No. FTA-4100.

What is claimed is:

1. Isolated DNA encoding the BsaWI restriction endonuclease, wherein the isolated DNA is obtainable from *Bacillus stearothermophilus* W1718.

2. A recombinant DNA vector comprising a vector into which a DNA segment encoding the BsaWI restriction endonuclease has been inserted.

3. Isolated DNA encoding the BsaWI restriction endonuclease and BsaWI methylase, wherein the isolated DNA is obtainable from ATCC No. FTA-4100.

4. A vector which comprises the isolated DNA of claim 3.

5. A host cell transformed by the vector of claim 2 or 4.

6. A method of producing recombinant BsaWI restriction endonuclease comprising culturing a host cell transformed with the vector of claims 2 or 4 under conditions suitable for expression of said endonuclease.

* * * * *

SEQUENCE LISTING

<160> NUMBER OF SEQ ID NOS: 17

<210> SEQ ID NO 1
<211> LENGTH: 1236
<212> TYPE: DNA
<213> ORGANISM: Bacillus stearothermophilus W1718
<220> FEATURE:
<221> NAME/KEY: CDS
<222> LOCATION: (1)..(1236)
<223> OTHER INFORMATION:

```
<400> SEQUENCE: 1 atg act aga cga tta cac att ata gat tgt ttt tct ggg cct gga gga        48
Met Thr Arg Arg Leu His Ile Ile Asp Cys Phe Ser Gly Pro Gly Gly
1               5                   10                  15 atc tgt aca gga ttt cga gca gca gga ttt gaa act tta tta gct atc        96
Ile Cys Thr Gly Phe Arg Ala Ala Gly Phe Glu Thr Leu Leu Ala Ile
            20                  25                  30 gag ttg gta gaa tct tgt gta gaa aca tat acg gct aac cac aaa gat       144
Glu Leu Val Glu Ser Cys Val Glu Thr Tyr Thr Ala Asn His Lys Asp
        35                  40                  45 gtt cct gtt atc aat aaa gat atc cgt gat gta act gaa gaa gag gtt       192
Val Pro Val Ile Asn Lys Asp Ile Arg Asp Val Thr Glu Glu Glu Val
    50                  55                  60 aag cgt atc gta ggg aat cgt gta gtg gat ata ctt aca gct gga atg       240
Lys Arg Ile Val Gly Asn Arg Val Val Asp Ile Leu Thr Ala Gly Met
65                  70                  75                  80 cct tgc gag acg ttt agt aca gcg gga gca act tct cgt agt ttc tat       288
Pro Cys Glu Thr Phe Ser Thr Ala Gly Ala Thr Ser Arg Ser Phe Tyr
                85                  90                  95 gat cat cgt cag ttt tta tat cgt gaa gct att cgt ctt gct gat gct       336
Asp His Arg Gln Phe Leu Tyr Arg Glu Ala Ile Arg Leu Ala Asp Ala
            100                 105                 110 gta aat gca cgg atg att tta ttt gaa aac gtt cct ggt atc cag acg       384
Val Asn Ala Arg Met Ile Leu Phe Glu Asn Val Pro Gly Ile Gln Thr
        115                 120                 125 aag aaa gtg gca aaa gat agt gat cgt ttg att att gat gaa att tat       432
Lys Lys Val Ala Lys Asp Ser Asp Arg Leu Ile Ile Asp Glu Ile Tyr
    130                 135                 140 gat gat tta gcg aaa tac gga tac gtt cac cat ata tct acg ata tta       480
Asp Asp Leu Ala Lys Tyr Gly Tyr Val His His Ile Ser Thr Ile Leu
145                 150                 155                 160 aat gca gag gat ttt ggt gtt cct caa tca aga gag cgt ttt ttt att       528
Asn Ala Glu Asp Phe Gly Val Pro Gln Ser Arg Glu Arg Phe Phe Ile
                165                 170                 175 tta gcc agt cgt gaa aaa ttg gat tta cgt gtt cca gtt gct aaa aac       576
Leu Ala Ser Arg Glu Lys Leu Asp Leu Arg Val Pro Val Ala Lys Asn
            180                 185                 190 aga aaa att gtg acc gta gag gaa gca ttt ata gat tta cct gaa gaa       624
Arg Lys Ile Val Thr Val Glu Glu Ala Phe Ile Asp Leu Pro Glu Glu
        195                 200                 205 ccg aaa gaa acg att aat tct gca aag aag aag cta gag aat gga gag       672
Pro Lys Glu Thr Ile Asn Ser Ala Lys Lys Lys Leu Glu Asn Gly Glu
    210                 215                 220 gaa att gag gta gaa caa tat aaa gac att gat tct gct tac agc aag       720
Glu Ile Glu Val Glu Gln Tyr Lys Asp Ile Asp Ser Ala Tyr Ser Lys
225                 230                 235                 240 ctt atg aag gat agg gat ttc tgg aag ttt gag aag aaa gaa tta gca       768
Leu Met Lys Asp Arg Asp Phe Trp Lys Phe Glu Lys Lys Glu Leu Ala
                245                 250                 255 ttg aca tat cat ttc gct cct gtt cat cga aaa ggg act atc aaa cgt       816
Leu Thr Tyr His Phe Ala Pro Val His Arg Lys Gly Thr Ile Lys Arg
            260                 265                 270 ttt gaa atg att aaa cag ggg gaa gga ttg aaa gat cta ttc gat aag       864
Phe Glu Met Ile Lys Gln Gly Glu Gly Leu Lys Asp Leu Phe Asp Lys
        275                 280                 285 ttg atg gct gaa cat gga cct gaa gaa atc gag cgg ctt cag aag gag       912
Leu Met Ala Glu His Gly Pro Glu Glu Ile Glu Arg Leu Gln Lys Glu
    290                 295                 300
```

-continued

```
aag ata att cca aat aag tgg tat atc caa aga aat cga aga tta tct     960
Lys Ile Ile Pro Asn Lys Trp Tyr Ile Gln Arg Asn Arg Arg Leu Ser
305             310                 315                 320 cct gat aag ccg agc gta act gta aca tca cat tgt tta agc gag ttg    1008
Pro Asp Lys Pro Ser Val Thr Val Thr Ser His Cys Leu Ser Glu Leu
            325                 330                 335 gtt cat ccg atc aaa aat cga gca ttg acg att cgt gag gtt gca cgt    1056
Val His Pro Ile Lys Asn Arg Ala Leu Thr Ile Arg Glu Val Ala Arg
        340                 345                 350 ttg caa agt ttt cct gat ttc tat gat ttc aaa ggc gga aaa ttt gta    1104
Leu Gln Ser Phe Pro Asp Phe Tyr Asp Phe Lys Gly Gly Lys Phe Val
    355                 360                 365 gca cct cat aaa gac cca caa cag gat aaa tat gaa cag att ggg gat    1152
Ala Pro His Lys Asp Pro Gln Gln Asp Lys Tyr Glu Gln Ile Gly Asp
370                 375                 380 gcc gtg cct cct ttg ttg gct tat cat tgg ggg ctg gtt ata aaa gaa    1200
Ala Val Pro Pro Leu Leu Ala Tyr His Trp Gly Leu Val Ile Lys Glu
385                 390                 395                 400 att ctt gaa gga gtt aaa gtt acg gag ggg gtc tag                    1236
Ile Leu Glu Gly Val Lys Val Thr Glu Gly Val
                405                 410
```

<210> SEQ ID NO 2
<211> LENGTH: 411
<212> TYPE: PRT
<213> ORGANISM: Bacillus stearothermophilus W1718

<400> SEQUENCE: 2

```
Met Thr Arg Arg Leu His Ile Ile Asp Cys Phe Ser Gly Pro Gly Gly
1               5                   10                  15

Ile Cys Thr Gly Phe Arg Ala Ala Gly Phe Glu Thr Leu Leu Ala Ile
                20                  25                  30

Glu Leu Val Glu Ser Cys Val Glu Thr Tyr Thr Ala Asn His Lys Asp
            35                  40                  45

Val Pro Val Ile Asn Lys Asp Ile Arg Asp Val Thr Glu Glu Glu Val
        50                  55                  60

Lys Arg Ile Val Gly Asn Arg Val Val Asp Ile Leu Thr Ala Gly Met
65                  70                  75                  80

Pro Cys Glu Thr Phe Ser Thr Ala Gly Ala Thr Ser Arg Ser Phe Tyr
                85                  90                  95

Asp His Arg Gln Phe Leu Tyr Arg Glu Ala Ile Arg Leu Ala Asp Ala
                100                 105                 110

Val Asn Ala Arg Met Ile Leu Phe Glu Asn Val Pro Gly Ile Gln Thr
            115                 120                 125

Lys Lys Val Ala Lys Asp Ser Asp Arg Leu Ile Ile Asp Glu Ile Tyr
        130                 135                 140

Asp Asp Leu Ala Lys Tyr Gly Tyr Val His His Ile Ser Thr Ile Leu
145                 150                 155                 160

Asn Ala Glu Asp Phe Gly Val Pro Gln Ser Arg Glu Arg Phe Phe Ile
                165                 170                 175

Leu Ala Ser Arg Glu Lys Leu Asp Leu Arg Val Pro Val Ala Lys Asn
                180                 185                 190

Arg Lys Ile Val Thr Val Glu Glu Ala Phe Ile Asp Leu Pro Glu Glu
            195                 200                 205

Pro Lys Glu Thr Ile Asn Ser Ala Lys Lys Leu Glu Asn Gly Glu
        210                 215                 220
```

```
Glu Ile Glu Val Glu Gln Tyr Lys Asp Ile Asp Ser Ala Tyr Ser Lys
225                 230                 235                 240

Leu Met Lys Asp Arg Asp Phe Trp Lys Phe Glu Lys Lys Glu Leu Ala
            245                 250                 255

Leu Thr Tyr His Phe Ala Pro Val His Arg Lys Gly Thr Ile Lys Arg
                260                 265                 270

Phe Glu Met Ile Lys Gln Gly Glu Gly Leu Lys Asp Leu Phe Asp Lys
            275                 280                 285

Leu Met Ala Glu His Gly Pro Glu Glu Ile Glu Arg Leu Gln Lys Glu
        290                 295                 300

Lys Ile Ile Pro Asn Lys Trp Tyr Ile Gln Arg Asn Arg Arg Leu Ser
305                 310                 315                 320

Pro Asp Lys Pro Ser Val Thr Val Thr Ser His Cys Leu Ser Glu Leu
                325                 330                 335

Val His Pro Ile Lys Asn Arg Ala Leu Thr Ile Arg Glu Val Ala Arg
                340                 345                 350

Leu Gln Ser Phe Pro Asp Phe Tyr Asp Phe Lys Gly Gly Lys Phe Val
            355                 360                 365

Ala Pro His Lys Asp Pro Gln Gln Asp Lys Tyr Glu Gln Ile Gly Asp
        370                 375                 380

Ala Val Pro Pro Leu Leu Ala Tyr His Trp Gly Leu Val Ile Lys Glu
385                 390                 395                 400

Ile Leu Glu Gly Val Lys Val Thr Glu Gly Val
                405                 410

<210> SEQ ID NO 3
<211> LENGTH: 819
<212> TYPE: DNA
<213> ORGANISM: Bacillus stearothermophilus W1718
<220> FEATURE:
<221> NAME/KEY: CDS
<222> LOCATION: (1)..(819)
<223> OTHER INFORMATION:

<400> SEQUENCE: 3 atg aat ttt ttt gag tat tgt atc agc acc tat gcc aag ata ttt gaa     48
Met Asn Phe Phe Glu Tyr Cys Ile Ser Thr Tyr Ala Lys Ile Phe Glu
1               5                   10                  15 gaa acg atg aat gca gtg ggt gat gaa cga gtt tcg caa aaa aag gca     96
Glu Thr Met Asn Ala Val Gly Asp Glu Arg Val Ser Gln Lys Lys Ala
            20                  25                  30 atc cgt gac aca atg atc tca gct atg aga gag ttt cca aat gtc gaa    144
Ile Arg Asp Thr Met Ile Ser Ala Met Arg Glu Phe Pro Asn Val Glu
        35                  40                  45 gcg gct gaa atc tgg aaa gct gtg tat tca gcc cat atg gat cgt aaa    192
Ala Ala Glu Ile Trp Lys Ala Val Tyr Ser Ala His Met Asp Arg Lys
    50                  55                  60 tca ggt ata gca gac cca gat att att caa aag gtc ata tca gcg gag    240
Ser Gly Ile Ala Asp Pro Asp Ile Ile Gln Lys Val Ile Ser Ala Glu
65                  70                  75                  80 aat agc tgg aaa aaa tcc agt gga cat gcc ttt gag gaa atg att aaa    288
Asn Ser Trp Lys Lys Ser Ser Gly His Ala Phe Glu Glu Met Ile Lys
                85                  90                  95 cta cta ggg aat agc agt tta gaa gaa tat gga atg cgt att ttg ctc    336
Leu Leu Gly Asn Ser Ser Leu Glu Glu Tyr Gly Met Arg Ile Leu Leu
            100                 105                 110 caa aaa gac tta aac atg atg att gaa aac caa gag att gca aat gaa    384
Gln Lys Asp Leu Asn Met Met Ile Glu Asn Gln Glu Ile Ala Asn Glu
        115                 120                 125
```

```
cca cgc gac ata aat tgg tta aaa gag caa att tct tct aac gta ttt        432
Pro Arg Asp Ile Asn Trp Leu Lys Glu Gln Ile Ser Ser Asn Val Phe
    130                 135                 140 gat ttg tac att aca gtg cgg aat aac gac aaa gag tat gtg ttt ggc        480
Asp Leu Tyr Ile Thr Val Arg Asn Asn Asp Lys Glu Tyr Val Phe Gly
145                 150                 155                 160 tgc att caa tcg aaa aca agc ata cgc gat aga gtc acc cgt gac cgt        528
Cys Ile Gln Ser Lys Thr Ser Ile Arg Asp Arg Val Thr Arg Asp Arg
                165                 170                 175 gag cct tcg atg aag gcg atg gaa gct ttc ttt tgg tca gtt gct atc        576
Glu Pro Ser Met Lys Ala Met Glu Ala Phe Phe Trp Ser Val Ala Ile
            180                 185                 190 tgt tta gat gga gac ttt tta aaa atg cca aaa ttt atc gca atg gta        624
Cys Leu Asp Gly Asp Phe Leu Lys Met Pro Lys Phe Ile Ala Met Val
        195                 200                 205 aat gga gga aca agt aat tat aga ttg aat ggc tgg cat ggt atg tat        672
Asn Gly Gly Thr Ser Asn Tyr Arg Leu Asn Gly Trp His Gly Met Tyr
    210                 215                 220 gta ttt tgg gac aag cca acg att gat cgt att tat ccg att gat atc        720
Val Phe Trp Asp Lys Pro Thr Ile Asp Arg Ile Tyr Pro Ile Asp Ile
225                 230                 235                 240 aac ctt gaa ttg ttt gta caa cat gca cgt gag gca gca gag gat tgg        768
Asn Leu Glu Leu Phe Val Gln His Ala Arg Glu Ala Ala Glu Asp Trp
                245                 250                 255 ctg cat aga cgg caa tgg ttt aat tat gag tgg aaa gca gga caa aaa        816
Leu His Arg Arg Gln Trp Phe Asn Tyr Glu Trp Lys Ala Gly Gln Lys
            260                 265                 270 taa                                                                    819

<210> SEQ ID NO 4
<211> LENGTH: 272
<212> TYPE: PRT
<213> ORGANISM: Bacillus stearothermophilus W1718

<400> SEQUENCE: 4

Met Asn Phe Phe Glu Tyr Cys Ile Ser Thr Tyr Ala Lys Ile Phe Glu
1               5                   10                  15

Glu Thr Met Asn Ala Val Gly Asp Glu Arg Val Ser Gln Lys Lys Ala
            20                  25                  30

Ile Arg Asp Thr Met Ile Ser Ala Met Arg Glu Phe Pro Asn Val Glu
        35                  40                  45

Ala Ala Glu Ile Trp Lys Ala Val Tyr Ser Ala His Met Asp Arg Lys
    50                  55                  60

Ser Gly Ile Ala Asp Pro Asp Ile Ile Gln Lys Val Ile Ser Ala Glu
65                  70                  75                  80

Asn Ser Trp Lys Lys Ser Ser Gly His Ala Phe Glu Glu Met Ile Lys
                85                  90                  95

Leu Leu Gly Asn Ser Ser Leu Glu Glu Tyr Gly Met Arg Ile Leu Leu
            100                 105                 110

Gln Lys Asp Leu Asn Met Met Ile Glu Asn Gln Glu Ile Ala Asn Glu
        115                 120                 125

Pro Arg Asp Ile Asn Trp Leu Lys Glu Gln Ile Ser Ser Asn Val Phe
    130                 135                 140

Asp Leu Tyr Ile Thr Val Arg Asn Asn Asp Lys Glu Tyr Val Phe Gly
145                 150                 155                 160

Cys Ile Gln Ser Lys Thr Ser Ile Arg Asp Arg Val Thr Arg Asp Arg
                165                 170                 175
```

```
Glu Pro Ser Met Lys Ala Met Glu Ala Phe Phe Trp Ser Val Ala Ile
            180                 185                 190

Cys Leu Asp Gly Asp Phe Leu Lys Met Pro Lys Phe Ile Ala Met Val
            195                 200                 205

Asn Gly Gly Thr Ser Asn Tyr Arg Leu Asn Gly Trp His Gly Met Tyr
            210                 215                 220

Val Phe Trp Asp Lys Pro Thr Ile Asp Arg Ile Tyr Pro Ile Asp Ile
225                 230                 235                 240

Asn Leu Glu Leu Phe Val Gln His Ala Arg Glu Ala Ala Glu Asp Trp
            245                 250                 255

Leu His Arg Arg Gln Trp Phe Asn Tyr Glu Trp Lys Ala Gly Gln Lys
            260                 265                 270

<210> SEQ ID NO 5
<211> LENGTH: 24
<212> TYPE: DNA
<213> ORGANISM: primer

<400> SEQUENCE: 5
cggcatcccc aatctgttca tatt                                            24

<210> SEQ ID NO 6
<211> LENGTH: 24
<212> TYPE: DNA
<213> ORGANISM: Primer

<400> SEQUENCE: 6
tgcctccttt gttggcttat catt                                            24

<210> SEQ ID NO 7
<211> LENGTH: 24
<212> TYPE: DNA
<213> ORGANISM: Sequencing Primer

<400> SEQUENCE: 7
ctgtacagat tcctccaggc ccag                                            24

<210> SEQ ID NO 8
<211> LENGTH: 24
<212> TYPE: DNA
<213> ORGANISM: Sequencing primer

<400> SEQUENCE: 8
taatgtgtaa tcgtctagtc atga                                            24

<210> SEQ ID NO 9
<211> LENGTH: 24
<212> TYPE: DNA
<213> ORGANISM: Sequencing primer

<400> SEQUENCE: 9
tgtacattac agtgcggaat aacg                                            24

<210> SEQ ID NO 10
<211> LENGTH: 24
<212> TYPE: DNA
<213> ORGANISM: Sequencing Primer
```

-continued

```
<400> SEQUENCE: 10
tatgtgtttg gctgcattca atcg                                      24

<210> SEQ ID NO 11
<211> LENGTH: 36
<212> TYPE: DNA
<213> ORGANISM: PCR Primer

<400> SEQUENCE: 11
gtgggatcca tgactagacg attacacatt atagat                         36

<210> SEQ ID NO 12
<211> LENGTH: 39
<212> TYPE: DNA
<213> ORGANISM: PCR primer

<400> SEQUENCE: 12
tgatacgcat gcctagaccc cctccgtaac tttaactcc                      39

<210> SEQ ID NO 13
<211> LENGTH: 51
<212> TYPE: DNA
<213> ORGANISM: PCR primer synthesized for PCR amplification

<400> SEQUENCE: 13
gaaggagcat gcggaggtaa ataaatgaat tttttgagt attgtatcag c         51

<210> SEQ ID NO 14
<211> LENGTH: 36
<212> TYPE: DNA
<213> ORGANISM: PCR primer synthesized for PCR Amplification

<400> SEQUENCE: 14
gccggatcca gacataggtt gaacatctaa ttatta                         36

<210> SEQ ID NO 15
<211> LENGTH: 54
<212> TYPE: DNA
<213> ORGANISM: PCR primer

<400> SEQUENCE: 15
gaaggatcta gaggatccgg aggtaaataa atgaattttt tgagtattg tatc      54

<210> SEQ ID NO 16
<211> LENGTH: 39
<212> TYPE: DNA
<213> ORGANISM: PCR primer

<400> SEQUENCE: 16
caatttctcg agagacatag gttgaacatc taattatta                      39

<210> SEQ ID NO 17
<211> LENGTH: 51
<212> TYPE: DNA
<213> ORGANISM: forward PCR primer which contains ribosome binding
      site, 6 bp prior to start codon

<400> SEQUENCE: 17 ccggatccg gaggtaaata aatgaattttt tttgagtatt gtatcagcac c        51
```